United States Patent [19]

Rosenbrook et al.

[11] Patent Number: 4,613,590

[45] Date of Patent: Sep. 23, 1986

[54] AMINO D-MANNO-2-OCTULOPYRANOSIDONATE CONTAINING COMPOUNDS, PHARMACEUTICAL COMPOSITIONS AND METHOD OF USE

[75] Inventors: William Rosenbrook, Libertyville; Paul A. Lartey; David A. Riley, both of Waukegan, all of Ill.

[73] Assignee: Abbott Laboratories, North Chicago, Ill.

[21] Appl. No.: 767,297

[22] Filed: Aug. 19, 1985

[51] Int. Cl.$^4$ .......................... A61K 31/70; C07H 5/06
[52] U.S. Cl. ...................................... 514/23; 536/1.1; 536/18.7; 536/53; 536/55
[58] Field of Search ............... 536/1.1, 17.2, 18.2, 536/18.7, 53; 514/23

[56] References Cited

U.S. PATENT DOCUMENTS 3,255,174  6/1966  Bannister ........................... 536/17.2
4,228,274 10/1980  Ponpipom et al. .................... 536/53
4,273,766  6/1981  Stanek .............................. 514/23

OTHER PUBLICATIONS

Charon, et al., "J.C.S." Perkin I pp. 1971–1977, 1980.
Collins, et al., "J.C.S. Chem. Comm." pp. 1139–1140, 1981.
Strain, et al., "J. Bio. Chem.", vol. 258, No. 22, pp. 13466–13477, 1983.
Strain, et al., "J. Bio. Chem.", vol. 258, No. 5, pp. 2906–2910, 1983.
Bigham, et al., "J. Med. Chem.", vol. 27, pp. 717–726, 1984.
Molin et al., "Tetrahedron Letters," vol. 26, No. 5, pp. 677–680, 1985.

*Primary Examiner*—Johnnie R. Brown
*Attorney, Agent, or Firm*—Steven F. Weinstock; Martin L. Katz

[57] ABSTRACT

Aminodeoxy derivatives of 3-deoxy-D-manno-2-octulosonic acid (KDO) are potent inhibitors of bacterial enzymes and a novel class of antibacterial agents.

10 Claims, No Drawings

AMINO D-MANNO-2-OCTULOPYRANOSIDONATE CONTAINING COMPOUNDS, PHARMACEUTICAL COMPOSITIONS AND METHOD OF USE

TECHNICAL FIELD

The invention relates to novel inhibitors of a component of gram-negative bacteria which are useful as gram-negative antibiotics and, more particularly, to inhibitors of the gram-negative bacterial enzyme, cytidine monophosphate ketodeoxyoctulosonic acid (CMP-KDO) synthetase.

BACKGROUND ART

Gram-negative bacteria possess a structural unit in their cell envelope called the outer membrane. This layer, which is not present in gram-positive bacteria, surrounds the cell wall and provides the organism with a major barrier to mammalian host defenses and to the penetration of antibiotics. The principal structural component of the outer membrane is lipopolysaccharide (LPS) and provides the major barrier function of the outer membrane.

For instance, erythromycin and vancomycin, which are active only at very high concentrations against gram-negative organisms, are about 100-fold more active against mutants with deficiencies in LPS biosynthesis. Mutants with deficiencies in the biosynthesis of certain regions of LPS are also susceptible to the lethal actions of elements of host defenses, such as lysozyme, deoxycholate and complement which are ineffective against normal gram-negative cells.

LPS itself is comprised of structural units that include a KDO oligosaccharide and a glycolipid (Lipid A), both of which have been shown to be essential to the viability of the bacterium. Thus, inhibitors of KDO and/or Lipid A biosynthesis represent targets for the discovery of novel gram-negative antibiotics.

SUMMARY OF THE INVENTION

The present invention is directed to compounds of the formula:

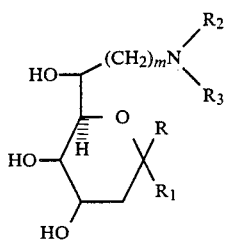

wherein R is hydrogen or hydroxy; $R_1$ is a carboxylic acid or $COR_4$ wherein $R_4$ is alkoxy or an amine; m is 1 or 2; and $R_2$ and $R_3$ are independently hydrogen, loweralkyl or acyl with the proviso that both $R_2$ and $R_3$ cannot simultaneously be acyl; and pharmaceutically acceptable salts thereof.

In particular, the most preferable compounds of the invention are those bearing an alpha or axial orientation of $R_1$ at the anomeric center.

As used herein, the term "loweralkyl" refers to straight or branched chain alkyl radicals from 1 to 6 carbon atoms including but not limited to methyl, ethyl, n-propyl, isopropyl, n-butyl, sec-butyl, t-butyl, n-pentyl, 2,2-methylbutyl.

As used herein, the term "amine" refers to $NR_5R_6$ wherein $R_5$ and $R_6$ are independently hydrogen or loweralkyl.

As used herein, the term "acyl" refers to

wherein $R_7$ is loweralkyl, amino-substituted loweralkyl or $CH_2NHCOCH_2NH_2$.

As used herein, the term "alkoxy" refers to straight or branched chain loweralkyl radicals containing from 1 to 6 carbon atoms and includes but is not limited to methoxy, ethoxy, n-propoxy, n-butoxy, 2-methoxy propyl.

In order to illustrate the manner in which the above compounds may be prepared and the properties of the compounds, Examples 1–9 are set forth below, which are not meant to limit or restrict the scope of the invention in any respect.

EXAMPLE 1

8-Amino-3,8-dideoxy-D-manno-2-octulosonate (a) Methyl (methyl-3-deoxy-8-O-p-toluenesulfonyl-D-manno-2-octulofuranosidon)ate Compound I, methyl (methyl 3-deoxy-D-manno-2-octulofuranosidon) ate, (7.2 g, 27.0 mmol), Charon D. & L. Szabo, J.C.S. Perkin I, 2369 (1979), was dissolved in 350 ml of dry pyridine. p-Toluene sulfonyl chloride [5.68 gm (29.8 mmol)] was added, followed by 0.33 g (2.7 mmol) of p-dimethylamino pyridine. The mixture was stirred at 0° C. for 2 hrs., then at room temperature overnight. The solvent was evaporated in vacuo. The residue was redissolved in 300 ml of $H_2O$ and partitioned with 3×300 ml portions of $CHCl_3$. The $CHCl_3$ extract was dried over anhydrous $MgSO_4$, filtered and evaporated in vacuo to afford 4.5 gm of the desired product, which was used without further purification. Yield 38%.

C-NMR in $CDCl_3$ (δppm from tetramethylsilane (TMS)); 21.6 (tosyl-$CH_3$), 45.2 (C-3), 51.7 (C-2 $OCH_3$), 53.0 (C-1 $OCH_3$), 70.5–70.8 (C-8), 71.3 (C-4), 72.1 (C-6), 72.9 (C-7), 87.7 (C-5), 106.7 (C-2), 128.1–145.1 (tosyl C), 170.5 (C-1).

(b) Methyl (methyl-8-azido-3,8-dideoxy-D-manno-2-octulofuranosidon)ate

Product 1a [25.9 g (61.6 mmol)] was dissolved in 350 ml of dimethylformamide (DMF). Twenty g (309.2 mmol) of $NaN_3$ was added and the mixture heated to 50° C. Heating was continued overnight. Solvent was removed in vacuo to yield a residue, which was redissolved in 500 ml of $CHCl_3$ and partitioned with 2×300 ml of $H_2O$. The combined aqueous layer was concentrated to 7.5 ml and extracted with 3×25 ml of EtOAc. The EtOAc extract was dried over anhydrous $NaSO_4$, filtered and evaporated to yield a syrup, which was purified by chromatography. Yield 35%.

C-NMR in $CDCl_3$ (δppm from TMS); 45.1 (C-3), 51.6 (C-2 $OCH_3$), 53.0 (C-1 $OCH_3$), 54.2 (C-8), 71.1–72.8 (C-4, C-6, C-7), 87.7 (C-8), 106.6 (C-2), 170.4 (C-1).

IR spectrum $CDCl_3$ (cm$^{-1}$); 1740 ($COOCH_3$), 2840 (C-$OCH_3$), 2105 ($N_3$).

(c) Methyl 8-azido-3,8-dideoxy-D-manno-2-octulofuranosidonic acid

To a solution of 0.126 g (0.43 mmol) of the product 1b in 30 ml of MeOH and 30 ml of H$_2$O, 63 mg of NaHCO$_3$ was added. The pH of the mixture was adjusted to 12 by gradual addition of 10N NaOH. The mixture was stirred at room temperature for 15 minutes and treated with the acidic resin HCR, to afford an acidic mixture. The mixture was filtered, methanol evaporated from the filtrate, neutralized with NH$_4$OH and the filtrate lyophilized to afford 117 mg of a white powder. Yield 92%.

C-NMR in D$_2$O ($\delta$ppm from sodium 3-trimethylsilylpropionate-2,2,3,3-d$_4$ (TSP)); 45.5 (C-3), 51.5 (C-2 OCH$_3$), 54.6 (C-8), 70.7-72.3 (C-4, C-6, C-7), 85.8 (C-5), 108.9 (C-2), 176.3 (C-1).

IR in KBr (cm$^{-1}$); 1410, 1605 (COO$^-$), 2105 (N$_3$).

(d) 8-Azido-3,8-dideoxy-D-manno-2-octulosonic acid

The product 1c (3.05 g, 10.4 mmol) was dissolved in 20 ml of 1 M trifluoroacetic acid and stirred at 50° C. for 90 minutes. Solvent was removed in vacuo to afford a solid residue. The residue was redissolved in 12 ml of H$_2$O and chromatographed over AG 1×8 [HCO$_3^-$] resin, using 0.2 M NH$_4$HCO$_3$ as eluent. Fractions containing the desired material were pooled, treated with HCR resin to render it acidic. The mixture was filtered and the filtrate neutralized by addition of NH$_4$OH, The neutral solution was lyophilized to afford a white powder. Yield 58%.

C-NMR in D$_2$O ($\delta$ppm from TSP); 34.4 (C-3), 54.8 (C-8), 66.9, 67.1, 68.7, 72.4 (C-4, C-5, C-6, C-7), 97.0 (C-2), 176.9 (C-1).

IR in KBr (cm$^{-1}$); 1410, 1610, (COO$^-$), 2110 (N$_3$). [$\alpha$]$_D$ = +37.7°.

(e) 8-Amino-3,8-dideoxy-D-manno-2-octulosonate

Compound 1d (1.0 g, 3.7 mmol) was dissolved in a mixture of 100 ml H$_2$O and 22 ml of 0.2 N HCl 0.11 gm of 5% Pd-C was added and the mixture hydrogenated at room temperature for 4 hrs. under 3 atmospheres H$_2$. The mixture was filtered and evaporated to yield a residue, which was purified by chromatography over silica gel, using the solvent system, CH$_2$Cl$_2$:MeOH:NH$_4$OH (2:5:2). Fractions containing the desired material were combined and solvent removed in vacuo. The residue was redissolved in 10 ml of H$_2$O and lyophilized to afford 0.18 gm of a white powder. Yield 20%.

H-NMR in D$_2$O ($\delta$ ppm from TSP); 1.9-2.5 (2H, m, CH$_2$-3), 3.0-3.2 (2H, m, CH$_2$-8), 3.4 (1H, m, CH-7), 3.8 (1H, m, CH-6), 4.0 (1H, m, CH-5), 4.2 (1H, m, CH-4).

C-NMR in D$_2$O ($\delta$ ppm from TSP); 34.2 (C-3). 43.3 (C-8), 66.1 (C-7), 66.6 (C-4), 66.9 (C-5), 74.0 (C-6), 97.0 (C-2), 176.9 (C-1);

MS (m/z) 238 (M+H)$^+$ for C$_8$H$_{15}$NO$_7$.

EXAMPLE 2
α-C-[1,5-anhydro-7-amino-2,7-dideoxy-D-manno-heptopyranosyl]-carboxylate

(a) Methyl [propylthio 4,5,7,8-tetra-O-acetyl-3-deoxy-D-manno-2-octulopyranosidon]ate Methyl[2,4,5,7,8-penta-O-acetyl-3-deoxy-α-D-manno-2-octulopyranoson]ate, [Unger F. M., *Adv. Carbohydr. Chem. Biochem.*, 38, 323 (1981). This reference also discusses the importance of KDO to the bacterial cell]. (2 g, 4 mmol) was dissolved in 50 ml of CH$_2$Cl$_2$ and the solution cooled in an ice-bath. Seven ml of a solution of 1.2 M TiCl$_4$ in CH$_2$Cl$_2$ was added. The mixture was allowed to warm to room temperature and stirred for 4 hrs. Anhydrous NaOAc (20 g) was added and the mixture stirred at room temperature overnight. The mixture was filtered and the residue washed with 100 ml CH$_2$Cl$_2$. The filtrate and washings were combined and evaporated in vacuo to afford 2 g of the glycosyl chloride. Sodium propyl thiolate was prepared by addition of 0.8 ml (8.8 mmol) of propanethiol to 5 ml of methanol containing 0.2 g (8.5 mmol) of sodium. The thiolate solution was then added to a suspension of the glycosyl chloride (2 g, 4.6 mmol) in 5 ml of methanol. The mixture was stirred for 45 minutes, filtered and evaporated to afford a residue, which was redissolved in 10 ml of dry pyridine. Acetic anhydride (10 ml) was added and the mixture stirred at room temperature overnight. The solution was evaporated to yield a syrupy residue, which was redissolved in 250 ml of CH$_2$Cl$_2$, washed with 200 ml of 5% aqueous NaHCO$_3$, 200 ml of aqueous NaCl, dried over anhydrous MgSO$_4$, and evaporated in vacuo to afford 1.4 g of a residue. The crude residue was purified by chromatography. Yield (36%).

C-NMR in CHCl$_3$ ($\delta$ppm from TMS); 13.5 (SCH$_2$CH$_2$CH$_3$), 20.7 (COCH$_3$), 22.8 (—SCH$_2$CH$_2$CH$_3$), 31.1 (C-3), 52.9 (CO$_2$CH$_3$), 62.4 (C-8), 64.8, 67.3, 67.9, 72.0 (C-4, 5, 7, 6), 84.0 (C-2), 168.7, 169.6, 169.8, 170.5, 170.6 (C=O); Anal. Calcd. for C: 50.20, H: 6.32, S: 6.70, Found: C: 49.86, H: 6.1, S: 6.60.

(b) Methyl α-C-[1,5-anhydro-2-deoxy-3,4,6,7-tetra-O-acetyl-D-manno-heptopyranosyl]-carboxylate To a solution of compound 2a (3.47 gm, 7.25 mmol) in ethanol (150 ml) was added Raney nickel (201 g, Grade #28). The reaction mixture was stirred for ½ hours at reflux, and allowed to cool to room temperature. The solution was then filtered and evaporated. Purification on silica gel (elution with toluene-ethyl acetate, 7:3) afforded a white solid. Yield 46%.

H-NMR in CDCl$_3$($\delta$ppm from TMS); 2.5-2.6(12H, 4s, COCH$_3$); 5.32(1H, s, H-4), 5.08(1H, m, H-6), 4.96(1H, M, H-3), 4.67 (1H, d, J$_{5,6}$=6 Hz, H-5), 4.44(1H, q, J$_{7,7'}$=12 HZ, J$_{6,7}$=2.4 HZ, H-7), 4.28(2H, m, H-1 and H-7);

C-NMR in CDCl$_3$($\delta$ppm from TMS); 20.6, 20.6, 20.7(CO CH$_3$), 26.2(C-2), 52.3(CO$_2$CH$_3$), 62.5(C-7), 64.9, 66.7, 68.0(C-3, C-4, C-6), 70.5(C-1), 72.2(C-5), 169.7, 169.8, 170.3, 170.6, 170.9(C=O); MS(m/z) 345(M-OAC); Anal. calcd. for C: 50.49, H: 5.98. Found C: 50.36, H: 5.97.

(c) Ammonium α-C-[1,5-anhydro-2-deoxy-D-manno-heptopyranosyl]-carboxylate

Compound 2b (635 mg, 1.57 mmol) was dissolved in 25 ml methanol. The mixture was treated with 6 ml of 5% aqueous NaHCO$_3$ for 68 hrs. at room temperature. Neutralization with ion exchange resin [AG50W-X8(H$^+$)], filtration and evaporation; afforded 300 mg of the ester, which was redissolved in 20 ml H$_2$O and treated with triethylamine at room temperature overnight. The solution was rendered acidic by treatment with AG50W-X8(H$^+$), filtered, neutralized with NH$_4$OH and lyophilized. The resulting white powder was purified by silica gel column chromatography (Solvent System; CHCl$_3$—CH$_3$OH-H$_2$O-NH$_4$OH (10:10:1:0.1) to afford a white solid. Yield 28%.

H-NMR in D$_2$O($\delta$ppm from TSP); 4.35(1H, d, $J_{1,2}$=6.4 Hz, H-1), 3.99(1H, d, $J_{3,4}$=2.7 Hz, H-4), 3.85-3.71 (4H, m, H-3,5,6,7), 3.55(1H, d, $J_{7,7'}$=8.1 Hz, H-7), 2.10(1H, dd, $J_{1,2eq}$=1.1 Hz, $J_{2eq,2ax}$=14.1 Hz, $J_{2eq,3}$=5.0 Hz, H-2$_{eq}$), 2.04(1H, m, $J_{1,2az}$=6.7 Hz, $J_{2ax,2eq}$=12.5 Hz, $J_{2ax,3}$=12.5 Hz);

C-NMR in D$_2$O ($\delta$ppm from TSP); 29.0(C-2), 64.5(C-7), 66.9(C-4), 67.4(C-6), 69.7(C-3), 74.3(C-1), 74.65(C-5), 178.9 (C=O); Anal. Calcd. for C 38.23, H 7.35, N 5.58; Found, C 38.31, H 6.99, N 5.48.

(d)
α-C-[1,5-Anhydro-7-azido-2,7-dideoxy-D-manno-heptopyranosyl]-carboxylate

To a solution of 800 mg (3 mmol) of Compound 2c in 50 ml dry methanol was added 2 gm of dry AG50WX8[H$^+$]. The mixture was stirred for 5 hrs, filtered and evaporated in vacuo to afford the crude methyl ester as an oil. The oil (743 mg, 3.15 mmole) was dissolved in 2 ml DMF. Triphenylphosphine (1.12 g, 4.27 mmol), 643 mg (9.8 mmol) of sodium azide and 760 mg (4.93 mmol) of carbon tetrachloride were added. The reaction mixture was allowed to stir overnight at room temperature. The mixture was filtered, and evaporated. The residue was taken up in water (50 ml), treated with triethylamine (5 ml) and the resulting mixture stirred for 18 hours. Evaporation and purification on silica gel (eluent CHCl$_3$—MeOH—H$_2$O—NH$_4$OH; 10:10:1:0.1) gave a syrup. Yield 33%.

C-NMR in D$_2$O ($\delta$ppm from TSP); 175.7 (CO), 74.9 (C-5), 72.9 (C-1), 68.4 (C-3), 66.5, 66.4 (C-6, C-4), 54.0 (C-7) and 27.9 (C-2).

H-NMR (D$_2$O) ($\delta$ppm from TSP); 4.45 (d, 1H, $J_{1,2}$=6.0 Hz, H-1), 3.86 (d, 1H, $J_{3,4}$=2.4 Hz, H-4), 3.77 (m, 1H, H-6), 3.67 (m, 1H, H-3), 3.52 (dd, 1H, $J_{6,7}$=2 Hz, $J_{7,7'}$=13.5 Hz, H7), 3.47 (d, 1H, $J_{5,6}$=9 Hz, H-5), 3.35 (dd, 1H, $J_{6,7}$=6 Hz, $J_{7,7'}$=13.5 Hz, H-7), 2.06 (dd, 1H, $J_{2e}$=4.5 Hz, $J_{2,2}$=13 Hz H-2$_e$) and 1.92 (m, 1H, $J_{2a,3}$=13 Hz, $J_{2a,2e}$=13 Hz, $J_{1,2a}$=6.9 Hz, H-2a).

(e)
α-C-[7-amino-1,5-anhydro-2,7-dideoxy-D-manno-heptopyranosyl]-carboxylate

A solution of compound 2d (2.33 g, 9.44 mmol) in water (100 ml) was hydrogenated at 4 atm. and room temperature with 20% Pd/C (0.23 g) for six hours. Filtration and evaporation gave a white solid. Yield 100%.

C-NMR in D$_2$O ($\delta$ppm from TSP); 178.1 (CO), 75.2 (C-5), 74.3 (C-1), 67.1 (C-3), 66.4 (C-6), 65.1 (C-4), 43.8 (C-7), and 28.7 (C-2)

H-NMR in D$_2$O ($\delta$ppm from TSP); 4.44 (d, 1H, $J_{1,2a}$=6.3 Hz, H-1), 4.08 (m, 1H, H-6), 3.97 (d, 1H, $J_{3,4}$=2.5 H-4), 3.73 (m, 1H, H-3), 3.48 (d, 1H, $J_{5,6}$=9 Hz, H-5), 3.24 (d, 2H, J=3.9 Hz, H-7), 2.5 (dd, 1H, $J_{2e,3}$=5 Hz, $J_{2a,2e}$=12.5 Hz, H-2e), 2.0 (t,1H,H-2a).

IR (KBr, cm$^{-1}$) 3420, 1590, 1410, 1110, 1060.

EXAMPLE 3

α-C-[1,5-anhydro-7-(glycyl-glycyl amino)-2,7-dideoxy-D-manno-heptopyranosyl]-carboxylate (a)
α-C-[1,5-anhydro-7-(N-carbobenzoxyglycyl-glycylamino)-2,7-dideoxy-D-manno-heptopyranosyl]-carboxylate A 235 mg (1.06 mmol) portion of compound 2 was dissolved in 3 ml of H$_2$O and 12 ml of tetrahydrofuran (THF). The solution was cooled in an ice bath for 10 minutes, and 212 mg (2.10 mmol) of triethylamine added. A 407 mg portion (1.05 mmol) of the p-nitro benzoyl active ester of N'-carbobenzoxy glycyl glycine was added. The mixture was stirred in the cold for 1 hour, then at room temperature overnight. The solution was evaporated. The residue was redissolved in 100 ml of H$_2$O and lyophilized. The product was purified by chromatography over LH-20 using MeOH as eluent. Fractions containing the desired material were combined and evaporated to give a syrup. Yield 77%.

MS; m/z 470 (M+H)$^+$ for C$_{20}$H$_{27}$N$_3$O$_9$.

(b)
α-C-[1,5-Anhydro-2,7-dideoxy-7-(glycyl-glycylamino)-D-manno-heptopyranosyl]-carboxylate A 440 mg (0.771 mmol) portion of compound 3a was hydrogenated under 3 atmospheres of hydrogen in the presence of 88 mg of 20% Pd/C in 50 ml of H$_2$O for four hours. Filtration and lyophilization of the filtrate afforded the triethylammonium salt of the desired compound. Yield 88%.

Anal. C$_{18}$H$_{36}$N$_4$O$_8$ Calcd. for: C: 49.52, H: 8.31, N: 12.84, Found C: 49.38, H: 8.25, N: 12.44, MS; m/z 336 (M+H)$^+$ for C$_{12}$H$_{21}$N$_3$O$_8$.

EXAMPLE 4

8-Methylamino-3,8-dideoxy-D-manno-2-octulosonate (a)
Methyl(3-deoxy-4,5:7,8-di-O-isopropylidine-D-manno-2-octulopyranoson)ate Ammonium KDO (20.0 g, 78.4 mmol) and 40 g of dry AG50W-X8(H$^+$) cation exchange resin were placed in a mixture of 400 ml dry methanol and 400 ml 2,2-dimethoxy propane and the reaction stirred at room temperature for 20 hours. The mixture was filtered and the solvents evaporated to give a residue which was purified by chromatography. Yield 33%.

MS (m/z) 317 (M-CH$_3$)$^+$ for C$_{15}$H$_{24}$O$_8$.

(b) Methyl(methylthiomethyl 3-deoxy-4,5:7,8-di-O-isopropylidene-D-manno-2-octulopyranosidon)ate Compound 4a(7.9 g, 24 mmol) was dissolved in a mixture of 100 ml dimethylsulfoxide and 100 ml acetic anhydride and the reaction stirred at room temperature for 18 hours. The mixture was diluted with 200 ml ethyl acetate and washed twice with 400 ml water and twice with 100 ml saturated sodium chloride solution. The organic phase was evaporated to a residue which was further purified by chromatography. Yield 84%.

C-NMR in CDCl$_3$($\delta$ppm from TMS): 14.7(s CH$_3$); 24.9 and 25.5[C(CH$_3$)$_2$]; 32.7(C-3); 52.5(CO$_2$CH$_3$); 66.9(C-8); 67.6(OCH$_2$S); 70.0(C-4); 71.9(C-7); 72.1(C-5); 73.9(C-6); 97.0(C-2); 109.3[O$_2$C(CH$_3$)$_2$]; 168.9(C-1).

MS (m/z) 377 (M-CH$_3$)$^+$ for C$_{17}$H$_{28}$O$_8$S.

(c) Methyl(methylthiomethyl 3-deoxy-4,5:7,8-di-O-isopropylidene-D-manno-2-octulopyranosidon)ate Compound 4b (2.1 g, 5.4 mmol) was dissolved in 500 ml methanol and treated with 75 ml 2M trifluoroacetic acid with stirring for 4.5 hours. The mixture was neutralized with an (OH$^-$) ion exchange resin, filtered, treated with 25 g sodium bicarbonate and the solvent removed by evaporation. The residue was taken up in 250 ml methylene chloride, washed once with 50 ml saturated sodium chloride, filtered and evaporated to a syrup which was used without further purification. Yield 72%.

MS (m/z) 353 (M+H)$^+$ for $C_{14}H_{24}O_8S$.

(d) Methyl(methylthiomethyl 3-deoxy-4,5-O-isopropylidene-8-O-p-toluenesulfonyl-D-manno-2-octulopyranosidon)ate Compound 4c (0.68 g, 1.9 mmol) was dissolved in 20 ml pyridine and treated with 0.8 g (4.0 mmol) of p-toluene sulfonyl chloride followed by 48 mg of p-dimethylamino pyridine. After 18 hours at room temperature the solvent was removed by evaporation. The residue was reconstituted in 50 ml chloroform, washed four times with 25 ml each of saturated sodium chloride solution, dried, filtered and evaporated to be used without further purification. Yield 88%.

MS (m/z) 507 (M+H)$^+$ for $C_{21}H_{30}O_{10}S_2$.

(e) Methyl (methylthiomethyl 7,8-anhydro-3-deoxy-4,5-O-isopropylidene-D-manno-2-octulopyranosidon)ate Compound 4d (0.86 g; 1.7 mmol) was dissolved in 20 ml acetonitrile and treated with 4.2 ml (4.2 mmol) of a 1M solution of tetrabutylammonium fluoride in tetrahydrofuran with stirring at room temperature for 3 hours. The solvents were removed by evaportion to leave a residue which was taken up in 20 ml methanol, treated with Dowex MR-3 resin, filtered and evaporated to a residue which was used without further purification. Yield 0.73 g.

H-NMR in CDCl$_3$($\delta$ppm from TMS): 0.96(3H, t, SCH$_2$CH$_2$CH$_3$); 1.58(2H, m, SCH$_2$CH$_2$CH$_3$); 1.98(1H, t, H-3a); 2.51 (1H, q, H-3e); 2.58 2.75(2H, m, SCH$_2$CH$_2$CH$_3$); 2.79(1H, m, $J_{7,8'}$=2.3, $J_{8,8'}$=5.1 H$_z$); 3.35(1H, m, H-7); 4.15(1H, m, $J_{4,5}$=5.5 H$_z$); 4.28 (1H, m, $J_{3a4}$=8.6, $J_{3e,4}$=5.9 H$_z$).

MS (m/z) 334 (M)$^+$ for $C_{14}H_{22}O_7S$.

(f) Methyl (methylthiomethyl 3,8-dideoxy-4,5-o-isopropylidene-8-methylamino-D-manno-2- octulopyranosidon)ate Compound 4e (0.32 g; 1 mmol) was dissolved in 10 ml dry methanol and treated with 7 ml (7 mmol) of a 1 M solution of methylamine in methanol with stirring at room temperature for 18 hours. The solvents were removed by evaporation to leave a residue which was used without further purification. Yield 100%.

H-NMR in CDCl$_3$($\delta$ppm from TMS): 1.32 and 1.41[6H, S, C(CH$_3$)$_2$]; 1.94(1H, q, 3e); 2.81(1H, q, 3a); 3.51(1H, q, H-8); 3.68(1H, m, H-6); 3.72(1H, q, H-8'); 4.15(1H, m, H-7); 4.39(1H, m, H-5); 4.54(1H, m, H-4); 4.59(2H, d, OCH$_2$S).

MS (m/z) 366 (M+H)$^+$ for $C_{15}H_{27}NO_7S$.

(g) 8-Methylamino-3,8-dideoxy-D-manno-2-octulosonate

Compound 4f (0.38 g, 1 mmol) was dissolved in a mixture of 3 ml methanol and 20 ml 2M trifluoroacetic acid. The mixture was heated, with stirring at 65° for 90 min and the solvents then removed by evaporation. The residue was dissolved in 10 ml 1M ammonium hydroxide, stirred at room temperature for 1 hour and lyophilized. The residue was purified by silica gel chromatography using the solvent system, CH$_2$Cl$_2$-MeOH-NH$_4$OH(2:5:1). Evaporation of the desired fractions gave a white powder. Yield 11%.

C-NMR in D$_2$O($\delta$ppm from TSP) 33.3(C-3): 33.5(CH$_3$N);52.4(C-8); 64.9(C-7); 65.7(C-6); 66.1(C-4); 77.8(C-5); 95.7(C-2); 173.0(C-1).

MS (m/z) 252 (M+H)$^+$; (m/z) 250 (M-H)$^-$.

EXAMPLE 5

8-Dimethylamino-3,8-dideoxy-D-manno-2-octulosonate

(a) Methyl(methyl 8-amino-3,8-dideoxy-D-manno-2-octulofuranosidon)ate

Compound 1b (3.7 gm, 12.7 mmol) was dissolved in a mixture of 136 ml methanol and 64 ml 0.2M methanolic hydrochloric acid. The mixture was treated with 3 atm hydrogen over 1.2 g 5% Pd-C at room temperature for 4 hours. The mixture was filtered and evaporated to yield a residue, which was redissolved in 30 ml of water and extracted 3 times with 30 ml portions of ethyl acetate. The aqueous layer was lyophilized to provide 2.0 g of white powder which was used without further purification. Yield 52%.

C-NMR in CDCl$_3$($\delta$ppm from TSM): 45.1(C-3); 51.6(OCH$_3$); 53.0(CO$_2$CH$_3$); 54.2(C-8); 71.1(C-4); 71.5(C-6); 72.8(C-7); 87.7(C-5); 106.6(C-2); 170./4(C-1).

(b) Methyl 8-dimethylamino-3,8-dideoxy-D-manno-2-octulofuranosidonate

Compound 5a (1.2 g; 4.0 mmol) was dissolved in a mixture of 6 ml dry methanol and 25 ml dry acetonitrile. Paraformaldehyde (1.6 ml; 20 mmol) and sodium cyanoborohydride (0.36 g; 5.8 mmol) were added and the mixture stirred at room temperature for 4 hours. The reaction was neutralized with acetic acid and stirring was continued for 45 minutes. Triethylamine was then added to provide a pH of ~9 and the solvents were removed by evaporation to give a residue which was purified by chromatography. Yield 17%.

MS (m/z) 280 (M+H)$^+$ for $C_{11}H_{21}NO_7$.

(c) 8-Dimethylamino-3,8-dideoxy-D-manno-2-octulosonate

Compound 5b (150 mg; 0.54 mmol) in 5 ml of 1M acetic acid was heated, with stirring for 6 hours. Solvents were removed by evaporation and the residue was purified by chromatography over silica gel using the solvent system CH$_2$Cl$_2$:MeOH:NH$_4$OH (2:5:1). Yield 47%.

C-NMR in D$_2$O($\delta$ppm from TSP): 35.6(C-3); 43.9 and 44.0(CH$_3$N), 61.2(C-8); 64.2(C-7); 66.5(C-4); 66.7(C-5); 70.0(C-6); 97.2(C-2); 175.8(C-1).

MS (m/z) 267 (M+H)$^+$ for $C_{10}H_{21}NO_7$.

EXAMPLE 6

8-Ethylamino-3,8-dideoxy-D-manno-2-octulosonate

(a) Methyl(methylthiomethyl 3,8-dideoxy-8-ethylamino-4,5-O-isopropylidene-D-manno-2-octulopyranosidon)ate Compound 4e (0.32 g; 0.94 mmol) was dissolved in 10 ml methanol and treated with 1.2 g (14.9 mmol) of ethylamine hydrochloride in 5 ml methanol [hydrochloride first removed by treatment with SBR(OH−) resin]. The reaction was stirred for 3 hours at room temperature. Solvent was removed by evaporation to give a residue which was purified by chromatography. Yield 59%.

MS (m/z) 380 (M+H)+ for $C_{16}H_{29}NO_7S$.

(b) 8-Ethylamino-3,8-dideoxy-D-manno 2-octulosonate

Compound 6a (0.16 g; 0.42 mmol) was treated with 20 ml 15M $NH_4OH$ with stirring at room temperature for 2 hours. Solvent was removed by evaporation. The residue was then taken up in 15 ml 2M trifluoroacetic acid and stirred at 60° for 3 hours. The solvent was removed by evaporation to give a residue which was purified by silica gel chromatography using the solvent sytem, $CH_2Cl_2$-MeOH-$NH_4OH$ (2:5:1) lyophilization of the desired fractions gave a white solid. Yield 11%.

C-NMR in $D_2O$(δppm from TSP) 11.2($NCH_2CH_3$); 34.5(C-3); 40.2($NCH_2CH_3$); 51.0(C-8); 65.7(C-7); 66.8(C-6); 67.0(C-4); 74.2(C-5); 97.2(C-2); 157.3(C-1).

MS (m/z) 266 (M+H)+ for $C_{10}H_{19}NO_7$.

EXAMPLE 7

α-C-[1,5 Anhydro-8-amino-2,7,8-trideoxy-D-manno octopyranosyl] carboxylate

(a) Methyl(propylthio 3-deoxy-D-manno-2-octulopyranosidon)ate

Compound 2a (48.6 g; 102 mmol) was dissolved in 400 ml dry methanol and treated with 22 ml of a solution of sodium in methanol (1.8 g sodium in 36 ml methanol) with stirring at room temperature for 2 hours. The reaction was treated with HCR(H+) resin, filtered and evaporated to a syrup which was used without further purification. Yield 61%.

H-NMR in $D_2O$(δppm from TSP): 2.0(1H, t, H-3a); 2.5(1H, q, $J_{3a,3e}$=13.0, $J_{3a,4}$=12.5, $J_{3e,4}$=5.0 Hz); 3.8(1H, m, $J_{4,5}$=3.0 Hz); 4.0(1H, m, $J_{5,6}$=1.0 Hz); 3.4(1H, m, $J_{6,7}$=9.5 Hz); 3.9(1H, m, H-7); 3.7 and 3.8(2H, m, $J_{7,8}$=$J_{7,8'}$=$7_{8,8'}$=12.5 Hz).

MS (m/z) 311 (M+H)+ for $C_{12}H_{22}O_7S$.
$[\alpha]_D^{22}$=+22° (C=1.0 in MeOH).

(b) Methyl(propylthio-3-deoxy-8-O-p-toluene sulfonyl-2-octulopyranosidon)ate Compound 7a (10.0 g; 32.23 mmol) was dissolved in 400 ml pyridine and treated with 11 g (58 mmol) of p-toluene sulfonyl chloride in the presence of 0.4 g p-dimethylamino pyridine over a period of 30 hours. Solvent was removed by evaporation to give a residue which was purified by chromatography. Yield 17%.

C-NMR in $CDCl_3$(δppm from TSP):
13.5($SCH_2CH_2CH_3$); 21.7($ArCH_3$); 22.8($SCH_2CH_6CH_3$); 31.0($SCH_2CH_2CH_3$); 35.0(C-3); 52.9($CO_2CH_3$): 65.7(C-5); 67.0(C-7); 67.5(C-4); 72.1(C-8); 75.2(C-6); 83.9(C-2); 169.6(C-1).

(c) Methyl(propylthio 8-cyano-3,8-dideoxy-2-octulopyranosidon)ate

Compound 7b (2.4 g; 5.2 mmol) was dissolved in 200 ml dimethylsulfoxide and treated with 0.51 g (10 mmol) of sodium cyanide with stirring at 65° for 3 hours. The reaction was taken up in 200 ml ethyl acetate and extracted three times with 150 ml portions of saturated sodium chloride, dried and evaporated to a syrup which was purified by silica gel chromatography. Yield 36%.

C-NMR in $CDCl_3$(δppm from TSP):
13.4($SCH_2CH_2CH_3$); 22.7 ($SCH_2CH_2CH_3$); 23.4(C-8); 31.3($SCH_2CH_2CH_3$); 35.1(C-3); 53.0($CO_2CH_3$); 65.3(C-4); 65.5(C-7); 67.1(C-5); 77.7(C-6); 84.2(C-2) 118.5(CN); 169.7(C-1).

MS (m/z) 320 (M+1)+ for $C_{13}H_{21}NO_6$.

(d) Methyl(propylthio 9-amino-3,8,9-trideoxy-D-manno 2-nonulopyranosidon)ate Compound 7c (0.53 g; 1.7 mmol) was dissolved in 20 ml dry tetrahydrofuran under a nitrogen atmosphere and the mixture cooled to 0°. Mixture treated, by dropwise addition, with 16.5 ml (16.5 mmol) of a 1M solution of borane-tetrahydofuran complex. The reaction was stirred 1 hour at 0° then for 4 hours at room temperature. The reaction was cooled to 0° and quenched with 10 ml methanol. Solvents were removed by evaporation. The final residue was partitioned between water and ethyl acetate and the aqueous phase was lyophilized to give a solid which was used without further purification. Yield 73%.

MS (m/z) 310 (M+H)+ for $C_{12}H_{23}NO_6S$.

(e) α-C-[1,5 Anhydro-8-amino-2,7,8-trideoxy-D-manno octulopyranosyl]carboxylate Compound 7d (0.40 g; 1.2 mmol) in water (200 ml) was hydrogenated at 3 atm. and 60° with 2.4 g of #28 Raney nickel for 1 hour. The reaction mixture was filtered and evaporated to a residue (0.26 g) which was purified by silica gel chromatography using the solvent system $CHCl_3$-MeOH-$NH_4OH$ (1:2:1). The desired fractions were combined and evaporated to give a white solid. Yield 28%.

C-NMR in $D_2O$(δppm from TSP) 29.0(C-2); 31.8(C-7); 36.5(C-8); 67.0(C-3); 67.2(C-4); 67.6(C-6); 74.8(C-5); 76.3(C-1); 178.7(CO).

MS (m/z) 234 (M−H)− for $C_9H_{17}NO_6$.

EXAMPLE 8

Methyl α-C-[7-amino-1,5-anhydro-2,7-dideoxy-D-manno-heptopyranosyl]-carboxylate

(a) Methyl α-C-[1,5-anhydro-7-azido-2,7-dideoxy-D-manno-heptopyranosyl]-carboxylate Compound 2c (3 mmole) was dissolved in 50 ml dry methanol and treated with 2 g of dry AG50W-X8(H+) resin. The mixture was stirred for 5 hrs., filtered and evaporated in vacuo to give the crude methyl ester as an oil. The oil was dissolved in 2 ml dimethylsulfoxide and the solution was treated with triphenylphosphine (4 mmol), sodium azide (5 mmol) and carbon tetrachloride (5 mmol). After stirring overnight at room temperature the mixture was filtered and evaporated. The residue was purified by chromatography on silica gel.

(b) Methyl
α-C-[8-amino-1,5-anhydro-2,8-dideoxy-D-manno-heptopyranosyl]-carboxylate Compound 8a (2 mmol) was dissolved in 100 ml water and hydrogenated at 3 atm and room temperature with 20% Pd-C for six hours. Filtration and evaporation gave the desired product as a white powder.

EXAMPLE 9

α-C-[7-Amino-1,5-anhydro-2,7-dideoxy-D-manno-heptopyranosyl]-carboxamide (a)

α-C-[1,5-Anhydro-7-azido-2,7-dideoxy-D-manno-heptopyranosyl]-carboxamide

Compound 8a (2 mmol) was placed in a 25 ml tube with 5 ml of anhydrous liquid ammonia. The tube was sealed and heated at 40° C. with stirring for 4 hours. Solvent was removed by evaporation in vacuo and the resulting product used without further purification.

(b)

α-C-(7-Amino-1,5-anhydro-2-7-dideoxy-D-manno-heptopyranosyl)-carboxamide

Compound 9a (1.5 mmol) was dissolved in 100 ml water and hydrogenated at 3 atm and room temperature with 20% Pd-C for six hours. Filtration and lyophilization gave the product as a white powder.

TABLE I

| Example | R | $R_1$ | m | $R_2$ | $R_3$ | $I_{50}$ (mM) |
|---|---|---|---|---|---|---|
| 1 | OH | COOH | 1 | H | H | 0.310 |
| 2 | H | COOH | 1 | H | H | 0.007 |
| 3 | H | COOH | 1 | H | $COCH_2NHCOCH_2NH_2$ | 0.230 |
| 4 | OH | COOH | 1 | H | $CH_3$ | 0.081 |
| 5 | OH | COOH | 1 | $CH_3$ | $CH_3$ | 0.220 |
| 6 | OH | COOH | 1 | H | $CH_3CH_2$ | 0.070 |
| 7 | H | COOH | 2 | H | H | 0.0019 |
| 8 | H | $CO_2CH_3$ | 1 | H | H | |
| 9 | H | $CONH_2$ | 1 | H | H | |

TABLE II

| | Mouse Protection $ED_{50}$ (mg/kg) | | |
|---|---|---|---|
| Compound | Escherichia Coli | Serratia marcescens | Staphylococcus aureus |
| Example 1 | 25.0 | 30.0 | 100.0 |
| Example 2 | 3.1 | 6.3 | 100.0 |
| Example 3 | 6.3 | 12.5 | 100.0 |

The novel compounds of the present invention are potent inhibitors of the enzyme CMP-KDO synthetase and, accordingly, effective, gram-negative antibacterial agents. The biological properties of the compounds are summarized in Tables I and II.

The inhibition of CMP-KDO synthetase activity was measured in reaction mixtures buffered at pH 9.5 containing: 2 mM KDO, 5 mM magnesium cytidine triphosphate, and inorganic pyrophosphatase. The pyrophosphate generated during the course of enzyme reaction was cleaved by the pyrophosphatase to inorganic orthophosphate, the level of which was measured colorimetrically. The efficacy of the inhibitors was calculated from the extent they inhibited phosphate production compared to a control which did not contain inhibitor. Potency was assessed by determining the level of inhibitor required to inhibit the enzyme reaction by 50% under the conditions of the assay described above ($I_{50}$). A potent inhibitor is defined as one having an $I_{50}$ of 1 mM or less.

Antibacterial activity of the compounds were tested in a mouse protection assay against *Escherichia Coli* Juhl, *Serratia marcescens* and the gram positive bacterium *Staphylococcus aureus*. The compounds prevented death in mice infected with lethal doses of the gram-negative bacteria but not against infection by gram positive bacteria.

The compounds of the present invention can be used in the form of suitable salts such as, for example, sodium, potassium, calcium, magnesium, aluminum, ammonium, ceric, chromic, cobaltic, cupric, ferric, silver, zinc, and organic base salts. Also, the basic nitrogen-containing groups can be quaternized with such agents as loweralkyl halides, such as methyl, ethyl, propyl and butyl chloride, bromides and iodides, dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

Total daily dose administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable preparation, for example, sterile injectable aqueous or oleagenous suspensions may be formulated according to the known art using suitable dispersing or wetting agents and suspending agents. The sterile injectable preparataion may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

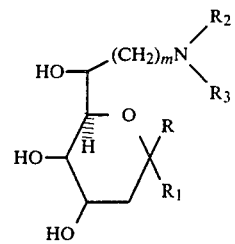

wherein R is hydrogen or hydroxy; $R_1$ is carboxylic acid or $COR_4$ wherein $R_4$ is alkoxy or $NH_2$; m is 1 or 2; and $R_2$ and $R_3$ are independently selected from hydrogen, loweralkyl or acyl with the proviso that $R_2$ and $R_3$ are not simultaneously acyl, and pharmaceutically acceptable salts thereof.

2. A compound as defined in claim 1 wherein $R_1$ is in alpha anomeric configuration.

3. A compound as defined in claim 2 wherein m is 1 and $R_1$ is carboxylic acid.

4. A compound as defined in claim 3 wherein R is hydrogen or hydroxy.

5. A compound as defined in claim 4 wherein $R_2$ and $R_3$ are independently hydrogen or $-CH_3$.

6. A compound as defined in claim 1 wherein R is hydrogen or hydroxy; $R_1$ is carboxylic acid in an alpha configuration and $R_2$ and $R_3$ are independently selected from hydrogen or loweralkyl.

7. A compound as defined in claim 6 wherein R is hydrogen, m is 2 and $R_2$ and $R_3$ are hydrogen.

8. A compound as defined in claim 6 wherein R is hydrogen, m is 1 and $R_2$ and $R_3$ are hydrogen.

9. A composition having antibacterial activity in pharmaceutical dosage form containing a diluent and a compound as defined in claim 1.

10. A method of treating bacterial infection in a patient comprising administering to a patient in need of such treatment a therapeutically effective amount of a compound as defined in claim 1.

* * * * *